United States Patent [19]

Salce et al.

[11] Patent Number: 5,241,973

[45] Date of Patent: Sep. 7, 1993

[54] FORMULATIONS AND APPLICATION METHODS FOR PERMANENT WAVE ENHANCEMENTS

[75] Inventors: Ludwig Salce, Greenwich; Andrew Savaides, Norwalk, both of Conn.

[73] Assignee: Shiseido, Tokyo, Japan

[21] Appl. No.: 877,089

[22] Filed: May 1, 1992

[51] Int. Cl.$^5$ .............................................. A45D 7/04
[52] U.S. Cl. .................................... 132/205; 132/202; 424/71; 424/72
[58] Field of Search ............... 132/202, 203, 204, 205, 132/209; 424/70, 71, 72

[56] References Cited

U.S. PATENT DOCUMENTS

| | | | |
|---|---|---|---|
| 4,369,037 | 1/1983 | Matsunaga et al. | 424/72 |
| 5,047,249 | 9/1991 | Rothman | 424/543 |
| 5,116,608 | 5/1992 | Yoshioka et al. | 424/72 |

Primary Examiner—Gene Mancene
Assistant Examiner—Frank A. LaViola
Attorney, Agent, or Firm—Melvin I. Stoltz

[57] ABSTRACT

By providing a composition for use with a conventional keratin reducing agent which comprises at least one mono or dimercaptopolyoxyethylene compound, a substantially improved and enhanced permanent wave is attained which provides a substantially increased long-lasting and durable hair set retention, as well as enhanced hair conditioning, sheen and manageability. In the preferred embodiment, the composition of the present invention is employed either as a post treatment after the application of a conventional hair keratin reducing agent or as an additive in the conventional reducing formulation. Furthermore, the preferred mono or dimercaptopolyoxyethylene compound employed preferably comprises a molecular weight ranging between about 200 and 800.

20 Claims, No Drawings

FORMULATIONS AND APPLICATION METHODS FOR PERMANENT WAVE ENHANCEMENTS

TECHNICAL FIELD

This invention relates to the art of permanently waving hair, and more particularly, to novel compositions and methods for imparting substantially increased, lasting, durable permanent hair set retention as well as enhanced conditioning sheen and manageability.

BACKGROUND ART

In view of the unique composition of hair fibers and the various changes in style and fashion, the permanent waving of hair has long been of particular interest. In order to best understand the various methods by which hair fibers can be styled or waved, it is important to remember that hair fiber is a proteinaceous material which has many chemical characteristics that relate to manageability, body, texture, static behavior, combability, and sheen. These characteristics may be altered with treatments of surface active agents, salts and polymers such as polysiloxanes, polyoxyalkylenes and polyvinyl pyrrolidones by altering the chemical structure of hair keratin.

It is well known that the three dimensional structure of hair keratin and its stability is related to hydrogen, coulombic, Van der Waals, and disulfide (S—S) bonds which link adjacent protein chains. These forces have also been described as comprising three major bonds that hold the configuration of the hair and are responsible for the strength of the hair. These three bonds are salt linkages, hydrogen bonds, and disulfide bonds. In dealing with these bonds, the hydrogen, coulombic, and Van der Waals forces are weak interactions and are highly dependent upon the water content in the hair keratin. Therefore, only temporary results are obtained by altering these weak interactions.

Because they are so numerous, the hydrogen bonds, involving the amino hydrogen and carbonyl oxygen of the amide linkages, are most important. Water, particularly in the monomolecular state, as occurs with moisture in the air (humidity), can weaken these bonds, by becoming a part of a hydrogen bonding structure. However, some of these hydrogen bonds are protected by hydrophobic bonds and will remain even when the hair is wet with water. More powerful hydrogen bond breakers, like high concentration of lithium bromide and urea are required for complete breakage of all hydrogen bonds.

As long as the hair fiber is dry, the strength of the hair fiber is not reduced. For example, a straight hair, wet with water and held by mechanical force in a curly configuration while drying will remain in a curly shape due to the formed hydrogen bonds and salt linkages, and it will not return to its straight shape so long as it remains dry. However, unless mechanically restrained, upon being wet with water, the hair will lose its curly configuration and become straight.

Normal or virgin hair is usually hydrophobic and many of the chemical treatments remove the natural hydrophobic components of hair. This decrease in hydrophobicity causes an increase in hair porosity resulting in increased rate of water absorption. The water-swollen hair is much more susceptible to mechanical stress such as stretching and breaking. Since hair is an elastic structure, the most common problem in hair setting, is the tendency to return to its natural shape. This tendency is highly accelerated under conditions of high humidity. The rate of return of hair into its natural configuration, is dependent on the method of hair deformation used.

Furthermore, when hair is set by the use of water alone, the hair will gradually lose its curly shape through the absorption of atmospheric moisture and the resulting rearrangement of the hydrogen bonds. This is due to the fact that in water, the dominant bonds are disulfide bond, while in the dry state, the dominant bonds are the salt linkages and the hydrogen bonds.

It is well know that hair fibers are composed of a unique protein called "keratin" which is distinguished by the fact that it contains a very significant amount of an amino acid (cystine) which contains the element sulfur in addition to the elements nitrogen, oxygen, carbon and hydrogen. In the natural synthesis of hair, the element sulfur covalently links intra or inter polypeptide chains (K) through two sulfur atoms (S—S) to give keratin protein (K—S—S—K). Only by chemical action can this covalent linkage be broken.

Since these disulfide bonds are much stronger than the bonds detailed above and are not affected by water, permanent results are obtained by altering the disulfide bonds through cleavage and recombination. In this way, a permanent configuration change of the hair is attained. However, chemical action is required in order for this disulfide linkage to be broken. In this regard, many prior art compositions have been developed for the cold permanent waving of hair. Typically, these prior art systems treat the hair with reducing agents which break the disulfide (cystine) linkage in the hair, while the hair is wound around a curling rod.

In general, permanent hair waving is usually carried out by subjecting the hair to reagents containing a free—SH group or thiol. These materials are also called mercaptans. In this treatment, the hair usually is either wrapped on the rods with water or the lotion containing the thiol, and then saturated with thiol lotion. The thiol waving agent acts to break the disulfide bonds within the hair fiber forming thiol groups in the hair protein and disulfide bonds between two thiol waving agent molecules. The chemistry involved in the reaction of the mercaptan with the cystine disulfide bonds in the hair fiber is illustrated by the following chemical equations (i), (ii) and (iii):

(i) 

(ii) 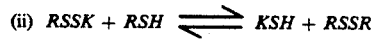

(iii) 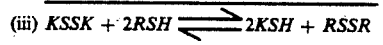

When a sufficient number of hair disulfide bonds have been broken, the hair is realigned to pair previously unpaired hair protein thiol groups opposite each other. At this point, the hair is rinsed, removing the unreacted thiol waving agent and any water soluble disulfide reaction product formed from it. Then, the hair is saturated with an oxidizing agent, or neutralizer, such as hydrogen peroxide or bromate salt, to reform disulfide bonds between the newly paired hair protein thiols, thereby giving the hair a new configuration or wave, or adding curl to the hair. By rebonding the sites of the reduced keratin in their new curled configuration, a permanent set which is impervious to water is established.

Much of the rebonding of the reduced sites is accomplished by the action of the chemical oxidizing agent, which is typically hydrogen peroxide, and can be illustrated by the following chemical reaction:

$$2 KSH + H_2O_2 \rightarrow KSSK + 2H_2O$$

In the art of permanent waving, there is much trial and error, with the hair being over-processed, in some instances. The characteristics of overprocessing are raspy feel to the hair or a bleaching of the natural underlying color. Structural evaluation of the hair fiber by instrumentation usually reveals that the structural integrity of the hair is lessened, which is evidenced by either an increase in the amount of cysteine and cysteic acid or a lessening of the cystine content relative to the hair not so processed.

Some detrimental effect to hair fiber is unavoidable, as the process of permanent waving involves controlled bond scission of the disulfide linkages within the keratin proteins. Recovery of these disulfides is the determining factor for the tightness of the curls and overall tensile strength. Typically, in order to reshape hair fibers into a lasting configuration, 20% to 50% of available disulfide bonds must be cleaved and reformed into the new configuration. If insufficient disulfide bonds are broken, the hair fiber will rapidly regain natural configuration.

In spite of the substantial effort that has occurred in the development of various permanent waving composition of this general nature, there has been a general inability to improve the holding power or curl configuration retention of "cold permanent waving" formulations. The typical problem encountered with the use of mercaptan reducing agents for the permanent waving of hair is that the permanency of the curl will not last until it is cut off. Instead, the curl relaxes slowly from the normal wear and tear of every day hair care. In this normal grooming process of shampooing, combing, drying and brushing the hair, the fibers are constantly being put under tension and exposed to forces that oppose the new disulfide and hydrogen bonds that were created in the new curl configuration.

In addition to longer curl retention, the industry has also sought to increase the luster, sheen, gloss and manageability of the hair, as well as provide a permanently waved head of hair which is soft, supple, and possesses a natural feel. However, these goals have not been fully attained.

Furthermore, permanent change in hair keratin coupled with operator error, provides inevitable damage to the hair fibers. This damage is measured by evaluating the tensile strength of hair keratin fibers caused by these chemical treatments. Therefore, it would be advantageous to provide treatments that would produce results of a permanent nature and minimum damage to hair keratin.

Since physical and chemical change in the keratin structure of hair fibers are observed during the deformation and relaxation of hair, researchers have tried to minimize the rate of hair relaxation caused by natural forces and water, utilizing treatments of naturally occurring or synthetic polymers. Some surface polymer treatments have had temporary effect on promoting cohesion and decreasing or retarding the rate of water uptake by the hair fiber, while other treatments have attained temporary improvement of such physical characteristics as sheen, manageability and strength. However, these prior art conditioning agents merely provide a temporary benefit and are incapable of satisfying the long-felt need for substantially permanent hair condition improvement.

Therefore, it is a principal object of the present invention to provide a composition for permanently waving hair fibers and a method for employing a permanent waving composition which is capable of imparting to the head of hair a durable, long-lasting permanent hair set retention.

Another object of the present invention is to provide a permanent wave composition and method of applying a permanent wave composition having the characteristic features described above which is capable of conditioning the hair fibers and improving physical properties of the treated hair such as shine, luster, softness, manageability, hair body, and thickness.

Another object of the present invention is to provide a permanent wave composition and method for applying a permanent wave composition to a head of hair having the characteristic features described above which is capable of imparting a long-lasting permanent wave or setting property to the hair, while substantially reducing hair damage caused during the reduction and oxidation processes.

A further object of the present invention is to provide a permanent wave composition and a method for applying a permanent wave composition to a head of hair having the characteristic features described above which is capable of improving the elastic and tensile properties of the hair fibers.

Another object of the present invention is to provide a permanent wave composition and a method for applying a permanent wave composition to a head of hair having characteristic features described above which is capable of attaining all of the desirable features while being employed during the actual reduction process or as a post-reduction step.

Other and more specific objects will in part be obvious and will in part appear hereinafter.

DETAILED DESCRIPTION

By employing the present invention, the prior art limitations and difficulties have been overcome and a long-lasting, permanently waved head of hair is attained, which also imparts to the hair fiber long lasting hair conditioning and enhanced physical properties such as shine, luster, softness, manageability and hair thickness. In order to attain these desirable and previously unattainable enhanced characteristics, a composition is employed during the permanent waving process which comprises mono or dimercaptopolyoxyethylene compounds. These compounds are employed to treat the hair keratin fibers, so that permanent physical and chemical properties are imparted thereto. Compounds coming within the scope of the present invention are defined by Formula I, detailed below:

FORMULA I $$R-OCH_2CH_2(-OCH_2CH_2)_n OCH_2CH_2O-R'$$

where n is about 5 to 20, and

| R,R' = | R,R' = |
|---|---|
| COCH$_2$SH | COCH$_2$N$^+$(CH$_3$)(CH$_3$)CH$_2$SH |
| = COCH$_2$CH$_2$SH | = —COCH$_2$CHSHCO— |
| = COCHSHCH$_3$ | = [—]CO[—]SH[—]N$^+$H$_3$ |
| = COCH$_2$CH$_2$CH$_2$SH | = COCHNH$_2$CH$_2$CH$_2$SH |
| = COCH(NH$_2$)CH$_2$SH | = COCH$_2$NHCH$_3$CH$_2$SH |
| | = COCHN$^+$HCOR''CH$_2$SH |
| = COCHOHCHOHSH | where R'' is any alkyl, and |
| = COCH$_2$NHCH$_2$CH$_2$SH | [—] is peptide chain |

By employing one or more of the mono or dimercaptopolyoxyethylene compounds defined by Formula I, in the manner detailed herein, highly desirable permanent waving properties are imparted into the hair keratin fibers. It has been found that by formulating permanent wave compositions, incorporating the compound defined by Formula I, a more permanent hair set is attained and damage that normally occurs from the reduction/oxidation process is prevented or substantially reduced. In addition, improved characteristics such as gloss, thickness, combability, softness, and body are imparted to the hair keratin fibers.

As detailed below, the compounds defined by Formula I can be employed in a separate treatment composition, which is applied to the hair after the application of the hair keratin reducing agent, or as part of the formulation of the reducing agent. Regardless of which application method or formulation is employed, the same desirable results are achieved.

These highly desirable results are believed to be attained due to the formation of new disulfide bonds between the hair keratin and the compounds defined by Formula I. By employing this invention, the compounds defined by Formula I are bonded permanently within the hair keratin and cannot be removed by shampooing. It has been found that the compounds defined by Formula I are irreversibly permanently bonded to the hair keratins via cross-sulfur linkages with cystine (reduced cysteine) and hair yielding polymeric mixed disulfides. It is these polymeric mixed disulfides that alter the structure of the hair keratin and change many of the chemical and physical properties of the hair fibers.

Possible mechanisms for the formation of these mixed disulfides can be represented by the equations detailed below, wherein equations are provided for the use of the compounds defined by Formula I as either a post-treatment or as part of the reducing agent.

Mechanism for Post Treatment Composition $KSSK + 2RSH \rightleftharpoons 2KSH + RSSR$ $KSH + HSBSH + H_2 \rightarrow KSSBSSK$ Mechanism for Modified Reducing Agent Formulation $KSSK + HSBSH \rightleftharpoons KSSBSH + KSH$ $KSSBSH + KSH + H_2O_2 \rightarrow KSSBSSK + KSSK$ $2KSSBSH + H_2O_2 \rightarrow KSSBSSBSSK$ wherein KSSK=Keratin; KSH=Reduced Keratin; HSBSH=Compounds of general Formula I; and KSSBSSK, KSSBSSBSSK=Mixed disulfides It should be noted that these are proposed mechanisms, and neither the scope of the present invention nor the embodiment of this invention, as detailed herein, should be limited to the theories proposed.

In order to obtain the enhanced results realized by employing the present invention, one or more compounds defined by Formula I are employed as part of the permanent waving process, either as a separate hair treatment composition or as one of the ingredients in the waving solution or reducing agent being employed. In either instance, it has been found that between about 1% and 50% by weight/volume of the Formula I compound is preferably employed in order to attain an effective, hair enhancing treatment composition.

One of the principal advantages achieved by the present invention is the substantial weight increase imparted to the hair fibers. In this regard, it has been found that hair fibers weight gain was realized when the hair was treated with compounds in accordance with Formula I of this invention, with the compounds having a molecular weight ranging between about 200 and 800.

This achievement is of particular importance, in that the body of the hair has long been one factor for which improvement has long been sought and has been unobtainable. It has now been found that by employing the present invention, not only is substantially long lasting curl retention realized, but also hair body and physical characteristics of the permanently waved hair are all substantially enhanced, in a manner which is retained within the actual hair structure and is not quickly lost, as is common with prior art compositions.

Although the present invention may be employed in a plurality of ways, one of the preferred methods for permanently bonding the compounds defined by Formula I of the present invention into the hair keratins is to reduce the hair keratin with conventional reducing agents, followed by the treatment of the reduced hair with a hair treatment composition incorporating one or more compounds in accordance with Formula I. Once the treatment is complete, the regeneration of the disulfide bonds follows, by employing a generally conventional neutralizer, such as peroxide, bromate, chlorite, oxygen, persulfate, etc.

In an alternate preferred method, compounds in accordance with Formula I are intermixed directly with the waving solution or reducing agent for application to the hair simultaneously with the waving solution or reducing agent. Once employed, a conventional neutralizer is used in the conventional manner.

In Table I, a preferred general formulation for the treatment composition is detailed.

TABLE I

| Treatment Composition | |
|---|---|
| Ingredient | % Wt. |
| Compound as defined by Formula I | 1%–50% |
| Ionic or Nonionic Detergent | 2%–6% |
| Fragrance | 0.25%–0.40% |
| Ammonium Hydroxide | adjust to pH as desired |
| Deionized water | q.s. to 100% |

Preferably, when a separate treatment composition is employed, the hair keratin is reduced with compositions such as ammonium thioglycolate, ammonium thiolactate, glycerylmonothioglycolate, glycerylthiolactate, cysteine, cysteamine, bisulfite, or other typical hair keratin reducing agents. In addition, the reducing agent is preferably applied to the hair for about 5 to 60 minutes either at ambient temperatures or at elevated temperatures ranging up to about 110° F. Furthermore, the preferred non-ionic or ionic detergent employed in the treatment composition comprises laureth-23.

Following the application of the reducing agent, the hair treatment composition, consisting principally of deionized water and one or more mono or dimercaptopolyoxyethylene compounds, as defined by Formula I, is prepared and applied to the hair.

Preferably, this hair treatment composition remains on the hair for between about 1 minute and 60 minutes. In the preferred embodiment, it has been found that the application time of 10 minutes is most desirable. It has also been found that the reducing agent can remain on the hair or, if desired, can be rinsed off prior to the application of the treatment composition. In formulating the treatment composition employed in accordance with this method, a pH range of between about 3.5 and 9.5 is preferred.

Once the treatment composition has been rinsed from the hair, the hair is neutralized to regenerate the disulfide bonds using a conventional neutralizer such as hydrogen peroxide, potassium bromate, or sodium chlorite.

In Table II, a preferred general formulation for the alternate preferred method is provided. In this alternate method, one or more compounds defined by Formula I are intermixed with the waving solution or reducing agent with the pH of the resulting composition being maintained between 6.8 and 9.5. Preferably, the quantity of the compounds of Formula I intermixed with the waving lotion or reducing agent ranges between about 1% and 35% by weight/volume of the final composition. In addition, this modified reducing composition is applied to the hair and allowed to remain for between about 5 to 60 minutes either at ambient temperatures or at elevated temperatures ranging up to about 110° F. Then, the modified reducing agent is rinsed from the hair, and is neutralized in the normal manner.

TABLE II

| Ingredient | Treatment Composition % Wt. |
| --- | --- |
| Reducing Agent (i.e., AMTG, GMTG) | 4%-25% |
| Compound as defined by Formula I | 1%-35% |
| Ionic or Nonionic Detergent | 2%-6% |
| Fragrance | 0.25%-0.40% |
| Ammonium Hydroxide | adjust to pH as desired |
| Deionized water | q.s. to 100% |

It has been found that regardless of which method is employed, substantially enhanced, permanently waved hair is attained. As detailed above, the use of the present invention not only provides improved physical characteristics, such as gloss, combability, and softness, but also substantially increases curl retention or hair set permanency. In addition, substantially improved and increased hair fiber weight, thickness, and body is also obtained, thereby providing the hair with results heretofore incapable of being realized. In this way, the present invention achieves a long sought, optimizing hair treatment wherein highly desirable properties are permanently imparted to the hair fibers for long term enjoyment by the consumer.

BEST MODE FOR CARRYING OUT THE INVENTION

In order to substantiate the versatility and substantial hair enhancements achieved by employing the compositions of the present invention, as well as by employing the methods of application of this invention, the following examples are presented. In the following disclosure, the universality of the present invention is fully detailed, along with its ability to permanently wave hair with substantially improved, long lasting, physical enhancements and characteristics permanently bonded therein. It is to be understood, however, that these examples are intended as a teaching of the best mode for carrying out the present invention and are not intended to limit, in any manner, the breadth of this discovery.

In order to prove the efficacy of the present invention and clearly establish that the polymeric mixed disulfides of this invention are effectively and irreversibly permanently bonded to the hair keratin via cross-sulphur linkages, the two preferred methods were employed to permanently wave numerous test hair tresses.

EXAMPLE I

In testing the use of a separate treatment composition, various formulations for the treatment composition were prepared, with each formulation being made in accordance with the ranges detailed in Table I. In each of the tests employing this method, the hair was first shampooed and then rolled onto styling rollers. Then, the waving lotion or reducing agent was applied and allowed to stand for 20 to 30 minutes. The hair was then rinsed and blotted to remove excess water.

Once the waving lotion or reducing agent had been rinsed from the rolled hair, 10 grams of the waving composition was applied to the hair tresses and allowed to stand for 10 minutes. Following this time period, the hair tresses were towel blotted, followed by the application of the desired neutralizer. The neutralizer was allowed to stand on the hair for 5 to 7 minutes. Finally, the hair was rinsed and styled as desired.

EXAMPLE II

In testing the efficacy of the alternate preferred application method, numerous different mono or dimercaptopolyoxyethylene compounds as defined by Formula I were employed directly with the waving lotion or reducing agent, in accordance with the formulation detailed in Table II. In permanently waving the head of hair, each of the tests were conducted with the hair tresses being first shampooed and then rolled onto a styling roller. Then, 10 grams of the particular compound in accordance with Formula I was added into the waving lotion or reducing solution and applied to the hair. This resulting composition was allowed to stand on the hair for about 20 to 30 minutes. After this time period, the hair tresses were rinsed and blotted to remove excess water.

Next, the desired neutralizer was applied to the hair tresses and allowed to stand for 5 to 7 minutes. Once this time period was achieved, the hair was rinsed and styled as desired.

Upon completion of the permanent waving process in all of the tests conducted using both the methods of Example I and Example II, weight gain of the hair tresses was determined. In obtaining this information, the hair tresses were rinsed thoroughly and carefully with water after the neutralization step and blotted to remove excess water, at ambient temperature. Then, the tresses were placed under vacuum in a desiccator containing silica gel. The weight of the tresses was monitored at various time intervals and the weight was recorded when no further change in weight was observed.

This same procedure for drawing the hair tresses to a constant weight was also used prior to treatment by the methods defined in Examples I and II as well as by that of controlled samples. The results of this test program clearly show that when hair fibers were treated with compounds of Formula I having a molecular weight between about 200 and 800, hair fiber weight gain was realized in both the method of Example 1 and the method of Example II.

EXAMPLE III

Hair fibers were reduced with GMTG (glycerylmonothioglycolate) for 30 minutes at room temperature and treated with various compositions in accordance with Table I. In each instance, the composition contained 30% by weight of the compounds of Formula I with R and R' comprising $COCH_2SH$. The pH of each of the test compositions was held constant at 3.7.

Triplicate tests were made and the average percent weight change was recorded. The weight change observed from the different composition treatments is shown below in Table III.

TABLE III

| Molecular Weight | % Wt Change |
| --- | --- |
| 776 | +4.31 |
| 748 | +4.87 |
| 548 | +6.22 |
| 776/548 (3:1) | +4.84 |
| 776/548 (1:3) | +5.75 |
| control | −0.01 |

EXAMPLE IV

In order to determine the most effective concentration for the compounds of Formula I when employed as a separate treatment composition, various tests were conducted using compounds in accordance with Formula I wherein R, R' equaled $COCH_2SH$, having a molecular weight of 548. Each of the formulations was constructed to have a pH of 7.5 with the quantity of the compound of Formula I ranging between 2% and 50% by weight. Using the different formulations, triplicate tests were run using the method defined in Example I. In each test run, the hair fibers were reduced with GMTG for 30 minutes at room temperature. The results attained are detailed in Table IV.

TABLE IV

| % (W/W) | % Wt Change |
| --- | --- |
| 2.0 | +3.18 |
| 5.0 | +3.39 |
| 10.0 | +3.99 |
| 30.0 | +4.42 |
| 50.0 | +6.44 |

EXAMPLE V

In order to show the effect the pH of the hair treatment composition has on the formation of mixed disulfides, the next series of tests were conducted. The results of these tests clearly show that the behavior of the mixed disulfide formation is highly dependent upon the pH, with the formation of mixed disulfides increasing as the pH of the reaction medium decreases.

In conducting these test samples, treatment compositions in accordance with Table I were prepared, with 30% by weight of the compound of Formula I being employed and with R, R' equal to $COCH_2SH$, having a molecular weight of 548. The application method detailed in Example I was employed for each of the tests, with the only variation being the pH of the treatment composition. Triplicate tests were run for each different pH level and the weight gain of the hair fibers was determined for each test. The average results of this program are shown below in Table V.

TABLE V

| pH | % WT CHANGE |
| --- | --- |
| 3.69 | +6.44 |
| 7.50 | +4.42 |
| 8.10 | +3.69 |

As is apparent from a review of the results detailed in Table V, greater polymeric mixed disulfides are formed in the hair fibers at the lower pH. This result was confirmed by amino acid analysis of the hair where it was found that twice as many mixed disulfides were formed at a pH of 3.5 than were formed at a pH of 8.

EXAMPLE VI

In order to further prove the efficacy of the present invention, hair fibers were treated with compositions incorporating compounds of Formula I using both the method defined in Example I and the method defined in Example II, with the tensile strength of the resulting hair fibers being evaluated. In order to show the effect of the present invention on tensile strength, the 20% index of the hair fibers were measured.

As is well known, the 20% index is a measure of the hair fiber damage in the yield region and is defined as the force ratio of treated to untreated hair fiber at 20% elongation. This method is commonly used to evaluate the damage being imparted to hair fibers.

In the tests conducted using the present invention, it was found that the 20% index of the resulting hair fibers treated with the methods of Examples I and II unexpectedly revealed less damage to the hair fibers. This result is equivalent to an increase in tensile strength.

As detailed in Table VI below, the 20% index for hair keratin fibers is provided based upon the use of a 10% by weight concentration of the compounds of Formula I with a molecular weight of 548 and a pH of 4.0, and with R, R' equaling $COCH_2SH$. In the tests conducted using the method of Example I, both AMTG (ammonium thioglycolate) and GMTG were employed as the reducing agents. For each test condition, triplicate tests were run.

TABLE VI

| Reducing Agent | # Treatments | 20% Index |
| --- | --- | --- |
| GMTG | 0 | 0.72 |
| GMTG | 1 | 0.78 |
| AMTG | 0 | 0.69 |
| AMTG | 1 | 0.72 |

It was also found that the 20% index and the tensile strength properties of the hair fibers continued to improve and were much more pronounced after a multiple of treatment of the hair fibers with the compounds of Formula I. It is believed that this tensile strength improvement may be caused by either the cumulative weight gain observed from multi-treatments of the composition of the present invention and/or by the increased number of disulfide crosslinks formed.

In order to effectively measure the tensile strength of the hair, an Instron Apparatus Model 1120 was used with each of the samples detailed above with the resistance forces for each of the hair fibers being determined at 20% elongation under aqueous immersion conditions. The overall results attained from this elongation test are shown in Table VI. The values presented in this table represents the initial reading (prior to treatment) minus the final reading (after treatment) divided by the initial reading. As a result, values closest to 1.000 indicate stronger relative tensile properties.

EXAMPLE VII

As mentioned above, the hair fibers exposed to numerous treatments employing the compounds of Formula I of the present invention experienced cumulative weight gain. It was found that this cumulative weight gain of the hair fiber even persisted after several shampooings. This factor is of particular importance since the cumulative weight gain shows that the use of the compounds of Formula I of the present invention are permanently and irreversibly bonded to the hair keratin via mixed disulfide bond formations.

In Table VII, the cumulative weight gain of the keratin fibers is shown where the fibers were treated with 10% by weight concentrations of compounds of Formula I having a molecular weight of 548 with the composition having a pH of 4.0. The hair was reduced using GMTG and the method defined in Example I was employed. Triplicate test runs were conducted and the weight gain of the hair fibers was determined for each test run. The average of the results are shown in Table VII.

TABLE VII

| # Treatments | % Weight Gain |
|---|---|
| *5 | +3.20 |
| *7 | +5.26 |
| *10 | +9.23 |
| 5** | +5.91 |

*The fibers were shampooed one time after each neutralization
**The fibers were shampooed five times after each neutralization

EXAMPLE VIII

It has also been found that by employing the teaching of the present invention, increased hydrophobicity of the hair keratin fibers is realized and, as a result, the rate of water uptake is decreased. It is believed that the increase in hydrophobicity of the treated hair fibers is due to the incorporation of hydrophobic bonds of $-CH_2CH_2-O-CH_2CH_2$ or a decrease in the porosity of the hair fibers.

In Table VIII, the water absorption behavior of hair fibers treated with the compounds of Formula I are provided. In each of the tests conducted, the compounds in accordance with Formula I comprise a molecular weight (M.W) of 548 and 748, with the composition having a pH of 4.0. In addition, in each of the tests, GMTG was employed as the reducing agent and the method defined in Example I was employed. In determining the percent water uptake of the hair fibers, the determination was made after exposing the hair fibers for 24 hours to a 90% to 100% humidity environment.

TABLE VIII

| | % Water Uptake | |
|---|---|---|
| # Treatments | M.W. 548 | M.W. 748 |
| 0 | 68.0 | 68.0 |
| 1 | 64.0 | 63.0 |
| 2 | 50.0 | 58.0 |
| 3 | 34.0 | 49.0 |

EXAMPLE IX

In view of the results obtained showing the effect of the treated hair fibers on porosity and hydrophobicity, it is expected that an increase in the stability of the hair set should be obtained. In order to demonstrate the achievement of this expected results, several experiments were carried out on freshly pre-shampooed hair tresses. Each of the hair tresses were rolled on styling rollers and treated with GMTG as a reducing agent, using both the method defined in Example I and Example II.

In each of the test samples, 5" tresses weighing 2 grams each were employed and were shampooed with a shampoo, blotted and rolled onto styling rollers. The tresses were then treated as defined above in Examples I and II. Once treated, the tresses were blotted dry and placed in a 100% humidity chamber at 26.6° C. for equilibration.

After 45 minutes, the rollers were removed and the tresses suspended freely in front of a measuring panel, with the initial length of the tress being recorded. The panel containing the suspended tresses was then placed in a 100% humidity chamber at 26.6° C. and the relaxation of the tresses was monitored by recording the length of the tresses at different time intervals.

As detailed below in Table IX, the percent set retention or percent curl retention after 4 hours for both treated and untreated tresses were calculated at different time intervals. In each instance, triplicate tests were conducted and GMTG was employed as the hair reducing agent. As is clearly shown in Table IX, substantial improved results are obtained by employing the present invention.

TABLE IX

| | % CURL RETENTION AFTER DIFFERENT RELAXATION TIMES (hrs) | | |
|---|---|---|---|
| TEST | 1.5 | 3.0 | 4.0 |
| Control | 93.5 | 82.1 | 70.7 |
| Method of Example I | 98.4 | 93.8 | 93.8 |
| Method of Example II | 98.3 | 98.3 | 95.0 |

The overall procedure and importance of determining the % set/curl retention is described in detail in the publication *Set Relaxation of Human Hair* by P. Diaz and M. Wong, Journal of the Society Cosmetic Chemists, 34, 205-212 (1983). In providing this information, the percent curl retention was calculated from the following formula:

$$\% \text{ SET CURL RETENTION} = \frac{L - Lt}{L - Lo} \times 100$$

$L$ = length of the fully extended hair tress
$Lo$ = length of the hair at the onset of relaxation
$Lt$ = length of hair curl at time $t$, where $t$ is the elapsed time since rollers were removed L=length of the fully extended hair tress
Lo=length of the hair at the onset of relaxation
Lt=length of hair curl at time t, where t is the elapsed time since rollers were removed As is apparent from the data provided in Table VIII, both methods of treatment of this invention yield a much more stable permanent set in a high humidity environment than is obtained from untreated hair fibers. These results clearly show that the treated fibers have a 94% to 95% curl retention, where the untreated hair fibers have a 70% curl retention after four hours in the high humidity environment. This data proves that by employing the present invention, a much slower relaxation rate of set hair is realized with the hair fibers being substantially less adversely affected by water absorption.

In addition, the present invention provides additional benefits. Hair is not tacky or sticky, combability is improved, and the hair fibers are less susceptible to mechanical damage from external stress, such as brushing. Furthermore, hair treated with the composition of the present invention possesses a much fuller set, natural feel, thicker body, softness, shine, manageability, improved tensile strength, and retains the imparted hair style even under high humidity conditions. It has also been found that the benefits and advantages of the present invention are realized regardless of hair types or the use of different perms available in the market.

It will thus be seen that the objects set forth above, among those made apparent from the preceding description, are efficiently attained and, since certain changes may be made in carrying out the above methods and in the composition set forth without departing from the scope of the invention, it is intended that all matter contained in the above description shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Particularly, it is to be understood that in said claims, ingredients or compounds recited in the singular are intended to include compatible mixtures of such ingredients wherever the sense permits.

Having described our invention, what we claim as new and desire to secure by Letters Patent is:

1. A composition for use with conventional permanent waving formulations for imparting a long-lasting, durable permanent wave to hair comprising at least one mono or dimercaptopolyoxyethylene compound having the formula $$R-OCH_2CH_2(-OCH_2CH_2)_nOCH_2CH_2O-R'$$

where n is about 5 to 20, and $$R-OCH_2CH_2(-OCH_2CH_2O-)_n-CH_2CH_2CO-R'$$

where n is about 5 to 20, and

| R,R' = | R,R' = |
|---|---|
| COCH$_2$SH | COCH$_2$N$^+$(CH$_3$)(CH$_3$)CH$_2$SH |
| = COCH$_2$CH$_2$SH | = —COCH$_2$CHSHCO— |
| = COCHSHCH$_3$ | = [—]CO[—]SH[—]N$^+$H$_3$ |
| = COCH$_2$CH$_2$CH$_2$SH | = COCHNH$_2$CH$_2$CH$_2$SH |
| = COCH(NH$_2$)CH$_2$SH | = COCH$_2$NHCH$_3$CH$_2$SH |
|  | = COCHN$^+$HCOR"CH$_2$SH where R" is any alkyl, and [—] is peptide chain. |
| = COCHOHCHOHSH |  |
| = COCH$_2$NHCH$_2$CH$_2$SH |  |

2. The composition defined in claim 1, wherein the mono or dimercaptopolyoxyethylene compound is further defined as comprising a molecular weight ranging between about 200 and 800.

3. The composition defined in claim 1, wherein said composition is further defined as comprising
   A. between about 1% and 50% by weight of the mono or dimercaptopolyoxyethylene compound;
   B. between about 2% and 6% by weight of an ionic or nonionic detergent;
   C. between about 0.25% and 0.40% by weight of a fragrance; and
   D. water forming the balance.

4. The composition defined in claim 3, wherein said composition is further defined as comprising ammonium hydroxide in sufficient amount to adjust the pH of the composition to range between about 3.5 and 9.5.

5. The composition defined in claim 4, wherein the molecular weight of the mono or dimercaptopolyoxyethylene compound is further defined as ranging between about 200 and 800.

6. The composition defined in claim 4, wherein said composition is further defined as comprising a post treatment composition for application to the head of hair after the use of a conventional hair keratin reducing agent.

7. The composition defined in claim 6, wherein the hair keratin reducing agent is further defined as comprising one selected from the group consisting of ammonium thioglycolate, ammonium thiolactate, glycerylmonothioglycolate, glycerylthiolactate, cysteine, cysteamine, and bisulfite.

8. The composition defined in claim 3, wherein said composition is further defined as comprising
   A. between about 1% and 35% by weight of the mono or dimercaptopolyoxyethylene compound;
   B. between about 4% and 25% by weight of a hair keratin reducing agent;
   C. between about 2% and 6% by weight of an ionic or a non-ionic detergent;
   D. between about 0.25% and 0.40% by weight of a fragrance; and
   E. water forming the balance.

9. The composition defined in claim 8, wherein said composition is further defined as comprising ammonium hydroxide in sufficient quantity to adjust the pH of the composition to range between about 6.8 and 9.5.

10. The composition defined in claim 9, wherein the mono or dimercaptopolyoxyethylene compound is further defined as comprising a molecular weight ranging between about 200 and 800.

11. The composition defined in claim 10, wherein the hair keratin reducing agent is further defined as comprising one selected from the group consisting of ammonium thioglycolate, ammonium thiolactate, glycerylmonothioglycolate, glycerylthiolactate, cysteine, cysteamine, and bisulfite.

12. A method for substantially improving the durability and manageability of permanently waved hair comprising the steps of
    A. applying a hair keratin reducing agent to a head of hair in a substantially conventional manner;
    B. formulating a treatment composition by mixing
       a. between about 1% and 50% by weight of at least one mono or dimercaptopolyoxyethylene compound having the formula $$R-OCH_2CH_2(-OCH_2CH_2)_nOCH_2CH_2O-R'$$

where n is about 5 to 20, and $$R-OCH_2CH_2(-OCH_2CH_2O-)_n-CH_2CH_2CO-R'$$

where n is about 5 to 20, and

| R,R' = | R,R' = |
|---|---|
| COCH$_2$SH | COCH$_2$N$^+$(CH$_3$)(CH$_3$)CH$_2$SH |

-continued

| | |
|---|---|
| = COCH$_2$CH$_2$SH | = —COCH$_2$CHSHCO— |
| = COCHSHCH$_3$ | = [—]CO[—]SH[—]N$^+$H$_3$ |
| = COCH$_2$CH$_2$CH$_2$SH | = COCHNH$_2$CH$_2$CH$_2$SH |
| = COCH(NH$_2$)CH$_2$SH | = COCH$_2$NHCH$_3$CH$_2$SH |
| | = COCHN$^+$HCOR"CH$_2$SH |
| = COCHOHCHOHSH | where R" is any alkyl, and |
| = COCH$_2$NHCH$_2$CH$_2$SH | [—] is peptide chain, and | b. water forming the balance;

C. applying the treatment composition to the hair after the application of the reducing agent;

D. allowing the treatment composition to remain on the hair for between about 1 and 60 minutes;

E. rinsing the treatment composition from the hair; and

F. neutralizing the hair in a conventional manner.

13. The method defined in claim 12, wherein the treatment composition is further defined as being formed by also intermixing
   c. between about 2% and 6% by weight of an ionic or non-ionic detergent; and
   d. between about 0.25% and 0.40% by weight of a fragrance.

14. The method defined in claim 13, wherein the treatment composition is further defined as being prepared by also intermixing therein ammonium hydroxide in sufficient quantity to adjust the pH of the treatment composition to range between about 3.5 and 9.5.

15. The method defined in claim 12, wherein the reducing agent is further defined as being applied to the hair and allowed to remain on the hair for between about 5 and 60 minutes at a temperature ranging from between ambient and 100° F.

16. The method defined in claim 12, wherein the treatment composition is further defined as being allowed to remain on the hair for 10 minutes.

17. A method for substantially improving the durability and manageability of permanent waved hair comprising the steps of
   A. formulating a modified hair reducing agent by mixing
      a. between about 1% and 30% by weight of at least one mono or dimercaptopolyoxyethylene compound having the formula

where n is about 5 to 20, and

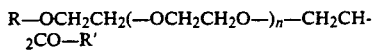

where n is about 5 to 20, and

| R,R' = | R,R' = |
|---|---|
| COCH$_2$SH | COCH$_2$N$^+$(CH$_3$)(CH$_3$)CH$_2$SH |
| = COCH$_2$CH$_2$SH | = —COCH$_2$CHSHCO— |
| = COCHSHCH$_3$ | = [—]CO[—]SH[—]N$^+$H$_3$ |
| = COCH$_2$CH$_2$CH$_2$SH | = COCHNH$_2$CH$_2$CH$_2$SH |
| = COCH(NH$_2$)CH$_2$SH | = COCH$_2$NHCH$_3$CH$_2$SH |
| | = COCHN$^+$HCOR"CH$_2$SH |
| = COCHOHCHOHSH | where R" is any alkyl, and |
| = COCH$_2$NHCH$_2$CH$_2$SH | [—] is peptide chain, | b. between about 4% and 25% by weight of a hair keratin reducing agent, and
   c. water forming the balance;

B. applying the modified hair reducing agent to the head of hair to be permanently waved;

C. allowing the modified hair reducing agent to remain on the hair for between about 5 and 60 minutes;

D. rinsing the modified hair reducing treatment composition from the hair; and

E. neutralizing the hair in a conventional manner.

18. The method defined in claim 17, wherein the modified hair reducing agent is further defined as being formulated by intermixing therewith
   d. between about 2% and 60% by weight of an ionic or non-ionic detergent,
   e. between about 0.25% and 0.40% by weight of a fragrance, and
   f. a sufficient quantity of ammonium hydroxide to adjust the pH of the composition to range between about 6.8 and 9.5.

19. The method defined in claim 17, wherein the modified hair reducing agent is further defined as being allowed to remain on the hair for between about 20 and 30 minutes.

20. The method defined in claim 17, wherein the mono or dimercaptopolyoxyethylene compound is further defined as comprising a molecular weight ranging between about 200 and 800.

* * * * *